United States Patent [19]

Cerami

[11] 4,330,299
[45] May 18, 1982

[54] ARTICLE AND METHOD FOR MEASURING GLUCOSE LEVEL IN BODY FLUIDS

[75] Inventor: Anthony Cerami, Flanders, N.J.

[73] Assignee: Evreka, Inc., Flanders, N.J.

[21] Appl. No.: 241,991

[22] Filed: Mar. 9, 1981

[51] Int. Cl.³ .................. G01N 33/66; G01N 33/52; G01N 33/58; G01N 31/22

[52] U.S. Cl. ................. 23/230 B; 23/901; 252/408; 422/56; 422/57; 422/61

[58] Field of Search ............... 23/230 B, 901; 422/56, 422/57, 61; 435/14, 805; 252/408

[56] References Cited

U.S. PATENT DOCUMENTS

| | | | |
|---|---|---|---|
| 3,061,523 | 10/1962 | Free | 23/901 X |
| 3,778,384 | 12/1973 | Dooley | 23/901 X |
| 3,791,988 | 2/1974 | Josef | 23/901 X |
| 3,897,213 | 7/1975 | Stevens | 23/230 R X |
| 4,287,028 | 9/1981 | Blass | 23/230 B X |
| 4,289,747 | 9/1981 | Chu | 23/230 B |

*Primary Examiner*—Sidney Marantz
*Attorney, Agent, or Firm*—David A. Jackson

[57] ABSTRACT

A method for measuring the level of glucose in animal body fluids such as blood and urine, comprises contacting the body fluid with a glucose indicator comprising a reversible complex of a carbohydrate component, a binding macromolecular component, and an indicator element bound to one of the components, and maintaining the body fluid in contact with the indicator for a period of time sufficient to permit any glucose present in the body fluid to displace the carbohydrate component in the complex, and to thereby release the indicator element to signify the presence of glucose. Preferably, the macromolecular component comprises one or more lectins, and the carbohydrate component may be one or more of the sugars for which testing is desired. The indicator element may be a dye or a color-forming radical, associated with either the lectin or the carbohydrate.

The glucose indicator may be prepared in strip form with either the lectin or the carbohydrate bound to an inert, insoluble substrate provided in kit form with a color chart keyed to identify specific sugars or concentrations thereof in the body fluid.

21 Claims, 1 Drawing Figure

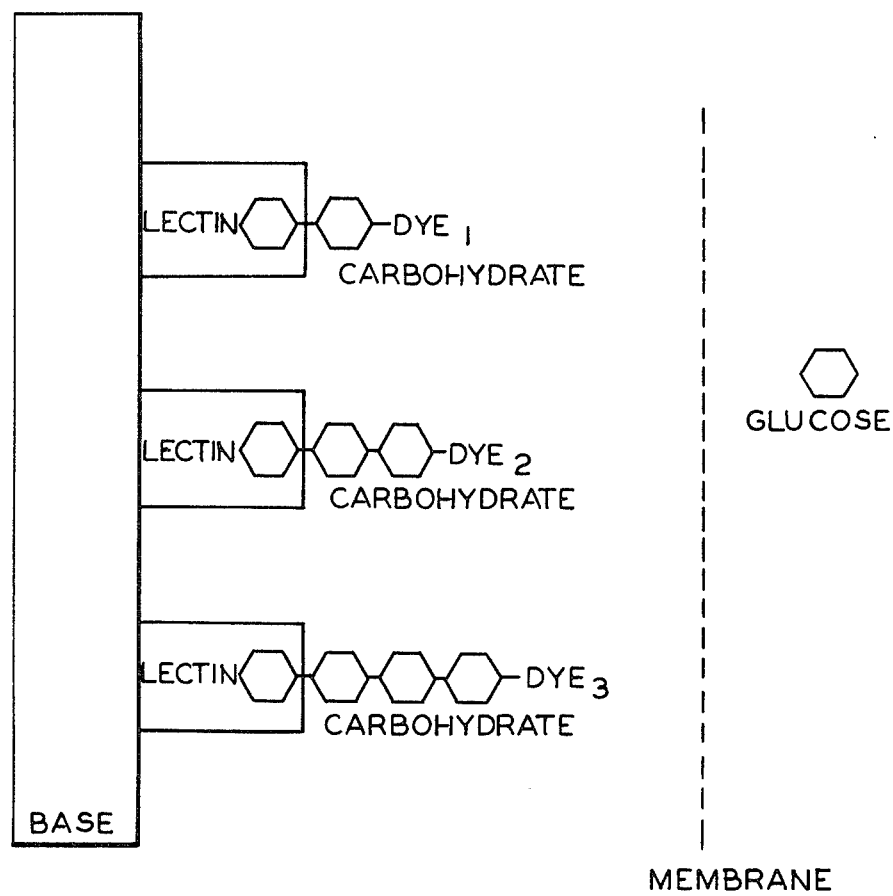

ARTICLE AND METHOD FOR MEASURING GLUCOSE LEVEL IN BODY FLUIDS

BACKGROUND OF THE INVENTION

1. Field of the Invention:

The present invention relates to a method and associated system for the measurement of glucose in animal body fluids.

2. Description of the Prior Art:

The detection and measurement of glucose in body fluids such as blood, urine and cerebro-spinal fluid, is an important consideration in the assessment of the functions of the body. Particularly, hypo- and hyperglycemic conditions, the result of abnormal variations in blood glucose level are often observed in patients receiving both emergency and routine medical attention, and because of their detrimental and potentially fatal effect, must be quickly and accurately measured to be properly treated.

Several methods have been used to attempt to properly monitor glucose levels. Two methods that are currently in wide use may be identified, respectively, as chemical and enzymatic. In the chemical method, a sample of body fluid likely to contain glucose, such as urine, is isolated and reacted with compounds that are capable of oxidizing glucose and producing a color change. This semiquantitative method is widely used to monitor patients having diabetes, to determine the amount of glucose spillage into the urine. The primary drawback of the chemical method, however, is that it is not specific for glucose and will give false readings with other sugars and body components with which the oxidants will react.

The enzymatic method for glucose measurement utilizes the enzyme glucose oxidase, which oxidizes available glucose with oxygen to form gluconic acid and hydrogen peroxide. The system associated with the enzymatic method includes a leuco dye with which the hydrogen peroxide by-product is coupled in a reaction that forms a specific color indicating the presence of glucose. The enzymatic method, while specific for glucose, is dificient as it is a kinetic analysis that depends upon temperature and time, and rerequires a specific apparatus to measure the amount of color-bearing composition formed at a given time.

The need therefore exists for a simple, accurate and dependable glucose measurement technique that will make instant and accurate analysis of glucose levels possible, by the individual patient as well as by the attending physicians.

SUMMARY OF THE INVENTION

Accordingly, a method for measuring the level of glucose in animal body fluids is disclosed which comprises contacting a portion of a given body fluid with a glucose indicator comprising a reversible complex of a carbohydrate component, a binding macromolecular component and an indicator element bound to one of the components. The sample of body fluid is maintained in contact with the glucose indicator for a period of time sufficient to permit the glucose present to displace the carbohydrate component in the reversible complex, whereby the indicator element is released to signify the presence of glucose.

The glucose indicator of the invention comprises the reversible complex of the carbohydrate component, the binding macromolecular component, and the indicator element. The carbohydrate component may comprise carbohydrate oligomers of differing size, and the macromolecular component may be carbohydrate-binding proteins such as lectins, with specific binding affinities for particular carbohydrates. The indicator element is preferably a dye or a color-forming radical, that may be associated or bound to either the carbohydrate oligomer or the lectin. In operation, the reversible complex between the carbohydrate oligomer and the lectin dissociates in contact with glucose present in the fluid sample, to the extent that such glucose is present, and this dissociation permits the indicator element to give a color reaction.

Specific lectins may be utilized in association with specific carbohydrates, to test for particular sugars present in the body fluid. The glucose indicator may comprise a variety or continuum of such lectin-carbohydrate oligomer complexes, each evidencing a variant indicator reaction responsive to the presence of differences in the identity or concentration of sugars present.

The glucose indicator may be prepared with one of the components irreversibly bound to a suitable and insoluble support, and enclosed within a selectively permeable membrane, and the final article may assume the form of a strip. A kit is likewise contemplated, comprising the glucose indicator in strip form and a color chart identifying the specific concentrations and identities of the sugars tested for.

The present invention offers a simple yet accurate and reliable method for determining glucose concentration in body fluids that provides medically significant quanitative identification of glucose. The dissociation of the indicator complex is less subject to variations due to time and temperature parameters, and is therefore more reliable. The indicator may be inexpensively prepared both alone and in kit form, and may be used even by individual patients.

Accordingly, it is a principal object of the present invention to provide a method for measuring the presence and concentration of glucose in animal body fluids.

It is a further object of the present invention to provide a method as aforesaid which yields prompt and reliable results.

It is a yet further object of the present invention to provide a method as aforesaid which utilizes an indicator comprising a reversible complex between a carbohydrate component and a macromolecular component, that operates in direct response to glucose concentration.

It is a yet further object of the present invention to provide a glucose indicator in strip form that is easily and rapidly utilized to indicate the presence of glucose in body fluid.

Other objects and advantages will become apparent to those skilled in the art from a consideration of the ensuing description, as well as the following drawing.

BRIEF DESCRIPTION OF THE DRAWING

The Figure is a schematic plan view illustrating the spatial relation of the components of the glucose indicator of the present invention.

DETAILED DESCRIPTION

The measurement of glucose concentrations in body fluid in accordance with the present invention makes use of a glucose indicator which, when contacted with a sample of the body fluid, quantitatively identifies the glucose by means of the reaction of an indicator element such as a dye. The glucose indicator comprises a reversible complex of a carbohydrate component, a binding maromolecular component and an indicator element associated with one of said components.

An important element of the present invention is the binding macromolecular component. The term "macromolecular component" as utilized herein, refers primarily to molecules that evidence reversible binding capability with other micro-or macro molecules. Examples of molecules meeting the foregoing definition include natural binding proteins, enzymes, regulatory proteins and synthetically modified binding molecules, such as chemically modified proteins. Of these, the natural proteins known as lectins are preferred herein.

Lectins are carbohydrate-binding proteins of plants and animals that exhibit a variety of specificities for carbohydrates (Lis et al, Ann. Review of Biochemistry, 42, 541 (1973); I. J. Goldstein and C. E. Hayes, Adv. in Carbohydrate Chemistry and Biochemistry, Vol. 35, R. S. Tipson and D. Horton, eds. (Academic Press, New York, 1978, pp. 128–341), herein incorporated by reference). Lectins, and in particular the lectin known as Concanavalin A, a Jack Bean lectin, exhibit a natural affinity for various sugars which, more particularly, is a function of the number of saccharide sub-units of the given sugar. For example, Concanavalin A, which is specific for glucose and mannose, will not bind with galactose; particularly, specificity is shown for $\alpha$-D-mannopyranose and $\alpha$-D-glucopyranose. Other lectins, such as soybean lectins show similar specificities; thus, soybean lectins are specific for $\beta$-D-N acetylgalactosamine and $\alpha$-D-galactose units, and wheat germ lectin is specific for $\beta$-D-N acetylglucosamine. The preferred lectin, Concanavalin A, is also observed to have an increased affinity for multiples of glucose up to 6.

The carbohydrate component preferably comprises a sugar, and includes the simple sugars or monosaccharides, as well as their low molecular weight condensation polymers, known as the oligosaccharides, that conventionally contain from two to nine monosaccharide units. Many of the sugars are naturally occurring, and may be found in animal body fluid. Particularly, a carbohydrate component may comprise glucose in the monomeric or oligomeric form; glucose oligomers may include other saccharides such as mannose and galactose, and may be either recovered from nature or synthetically prepared. The naturally occurring oligosaccharides are often associated with protein or lipid fractions, and may be utilized herein in such form.

The specific carbohydrate component useful in the present invention is chosen on the basis of its equivalence in affinity for the formation of the reversible complex with the macromolecular component, with the material or agent to be detected and measured by the present indicator. Thus, for example, as the lectin Concanavalin A has an increasing affinity for glucose in multiples up to 6, it would tend to favor glucose oligomers with greater numbers of monosaccharide units; correspondingly, this affinity would extend to concentrations of glucose in a fluid sample that would correspond in range. In particular, the corresponding range of glucose concentrations in body fluids lies within the physiological range of 10–400 mg/dl. Accordingly, and referring to the FIGURE, a glucose indicator could be prepared with a plurality of lectin molecules, each disposed on a substrate, and reversibly associated with carbohydrate components of differing size, representing a continuum of saccharide units corresponding to the physiological range of glucose Relatively low levels of glucose concentration would be unable to displace the higher oligomers, but would readily displace the oligomers of corresponding affinity, which in turn would permit the associated indicator element to signify the presence of glucose in that concentration. The exact operation of the reversible complex, and the indicator element, will be discussed hereinbelow.

The reversible complex constituting the indicator of the present invention comprises a reaction between the macromolecular component and the carbohydrate component, as generally noted above. This reaction must be reversible and non-covalent. The bonding that occurs between the respective components is caused by non-covalent forces such as hydrophobic, ionic hydrogen bonding forces and the like. Such interactions are known in the art, and their effects on molecular affinity and recognition have been described, for example, in Korolkovas, et al, "Essentials of Medicinal Chemistry", pp 44–81, John Wiley & Sons, 1976, and the particular reactions of proteins and carbohydrates has been reviewed in Goldstein, I. J. ed., *Carbohydrate-Protein Interaction*, ACS Symposium Series No. 88 (1979), both incorporated herein by reference. An example of a reversible interaction is the interaction between an enzyme and its substrate or a competitive inhibitor thereof.

As described earlier in brief, the present reversible complex between the carbohydrate component and the macromolecular component operates in a state of dynamic equilibrium, as the material in the body fluid being tested for, and the carbohydrate component compete for association with the macromolecular component. In the instance where the macromolecular component is a lectin, and the material under test is glucose at certain levels of concentration, a glucose indicator such as that described above and schematically illustrated in the FIGURE, participates in an equilibrium that arises between the glucose at the particular concentration and the reversible complex bearing a corresponding carbohydrate component, to complex with the lectin. The displacement of the carbohydrate component of a particular reversible complex permits the indicator associated with that complex, to signify the presence of the particular concentration of glucose. The location and function of the indicator element is discussed below.

The indicator element of the present invention may be associated with either the carbohydrate component or the macromolecular component, and serves the sole function of signifying the dissociation of these components, and the corresponding presence of glucose. In the present invention, the indicator component may be a color forming material such as a dye or a color forming radical that is freed or otherwise chemically altered by the dissociation of the carbohydrate and the macromolecular components, to produce a color-forming reaction. The indicator element may also include a compound or portion thereof that forms a precipitate upon such dissociation, and the invention therefore is not limited to color forming materials exclusively. For example, a dye such as an arylhydrazine may be reacted with the reducing end of a carbohydrate oligomer to form a stable addition product such as an arylosazone, which will give a color reaction when the carbohydrate component and the macromolecular component are dissociated. By utilizing different hydrazines in combination with different oligomers responsive to individual concentrations of glucose, it is possible to develop a mixture of ligands exhibiting variations in color formation and affinity for particular lectins, whereby different concentrations of glucose will cause the formation of differing color reactions. Referring again to the schematic FIGURE, the disposition of different dyes with different chain length oligomers illustrates the manner in which the discrete levels of glucose concentration in fluid samples can be identified.

The indicator element may be associated with the macromolecular component, rather than the carbohydrate component, however, with the same manner of operation. Thus, the specific dyes such as Rhodamine, isothiocyanate, 4 Dimethylaminoazobenzene-4'-sulfinyl chloride and the like, that are capable of reacting with proteins, may be incorporated onto the macromolecular components. In this embodiment, the carbohydrate component, rather than the macromolecular component would be fixedly attached to a substrate and the dissociation of the carbohydrate and the macromolecular component would set the latter free, permitting the attached dye to form its color reaction. The disposition of the respective components on the substrate will be discussed later on with reference to the preparation of the indicator of the present invention.

In a further embodiment, the indicator element may comprise a particular functional group that may be associated with the carbohydrate or the macromolecular component, and which would be capable of forming the colored complex with an immobilized dye included with the glucose indicator, when the respective component bearing the functional group is displaced. For example, a sulfhydryl group may be incorporated into the carbohydrate component, and would, upon its release, react with a number of reagents, such as 5,5'-dithiobis (2-nitrobenzoic acid), to develop a color.

In general, the method of the present invention comprises contacting the indicator herein described with a quantity of a animal body fluid, and maintaining the indicator in contact therewith for a period of time sufficient for the indicator element to signify the presence and quantity, if any, of the material being tested for, in the sample fluid. In particular, the analysis of body fluid for the presence of glucose in specific concentrations is conducted by placing such fluid in contact with the aforedescribed glucose indicator, and maintaining the fluid in contact for a period of time sufficient to enable the reversible complex between a particular macromolecular component and its corresponding carbohydrate component, to dissociate in favor of a complex involving the macromolecular component and the in vitro glucose, which latter event will be signified by the indicator element. In the instance where the glucose indicator comprises a lectin such as Concanavalin A reversibly bound to a glucose oligomer bearing a particular dye, the indicator would be placed in contact with a drop of body fluid which would be maintained in contact with the indicator for a period of time, such as, for example, up to five minutes, whereupon equilibrium between the glucose present and the reversible complex will have been reached, and the indicator element comprising the dye will have given its color reaction.

The glucose indicator of the present invention may be prepared as follows. The particular lectin or lectins chosen for use may be fixed to a suitable insoluble support, such as cellulose, agarose, plastic, glass and the like, by either covalent bonding or non-covalent adsorption. The technique of solid state immobilization of enzymes and other proteins or resins, films, test tubes, glass beads and the like are well known (see e.g., Zaborsky, C. "*Immobilized Enzymes*", CRC Press, Cleveland, 1973; Lowe, C. R. and Dean, P. D. G., "The Chemistry of Affinity Chromatography", *Affinity Chromatography*, John Wiley and Sons, N. Y., 1974; Axen, et al., U.S. Pat. No. 3,645,852; and Kraemer, et al., U.S. Pat. No. 4,039,413). For example, the lectin may be attached to a cellulose support by activation of the support with cyanogen halide, reaction with cyanuric acid, periodate oxidation, epoxide formation, and reaction with various bifunctional reagents, such as bis-oxinane, dimethyl adipimate, phenol-2, 4-disulfonyl chloride, and divinyl sulphone. Preferably, a cellulose strip is reacted with cyanogen bromide, and the thus activated cellulose strip is then incubated with Concanavalin A, and the reaction later stopped by the addition thereto of glycine.

While the foregoing procedure relates particularly to the affixation of the macromolecular component to a substrate, it is to be understood that the carbohydrate component may be similarly anchored by techniques equally well known in the art, so that the various mono- and oligosaccharides may be permanently bound to the substrate and reversibly associated with the respective lectins.

As noted earlier, the specific carbohydrate components may be either recovered from nature or synthetically prepared. Particular carbohydrates may be prepared by, for example, limited acid hydrolysis of mannin to form oligomers of varying length which are then separable by chromatography, to recover the specific oligosaccharides. After recovery of the carbohydrate components, they may either be fixedly bound to the substrate, or reacted with various dyes to form the conjugates illustrated schematically in the FIGURE. Thus, oligomers of varying chain length may bear different dyes as denoted, and as described in detail earlier.

Once both of the components are prepared with the indicator element affixed as desired, the carbohydrate and macromolecular components are brought in contact with each other, and establish the reversible complexes described earlier. After the reversible complexes are formed, the resulting glucose indicator, preferably in strip form, may be covered with a semipermeable membrane designed to permit glucose and the dye-carbohydrate complex to diffuse readily therethrough. A variety of such semi-permeable membranes are already well known for use in testing equipment of this type, and includes a variety of natural and synthetic resinous materials evidencing pore size, etc., condusive to this application.

Referring again to the FIGURE, the strip schematically shown would be placed in contact with the fluid sample, with the pores of the membrane sufficiently large to permit the passage of glucose therethrough to compete for the formation of a reversible complex with the support-bound lectin. Upon the displacement of the carbohydrate component by the glucose, the dye, such as "Dye 1" would be free to form a color reaction to signify its displacement, whereby an indication of the glucose concentration would be given.

In accordance with a further aspect of this invention, the glucose indicator, in strip form, would be provided in kit form, together with a suitable color chart, having thereon explanation of the respective colors and their significance in assessing test results. Thus, a series of colors would be outlined that would denote particular glucose concentration levels, so that the user of the kit would easily be able to determine and analyze the test results. The simplicity and speed of operation of the test method and associated kit would make it possible for patients as well as physicians to administer the test, and to understand its results; thus, in the instance of a person suffering from diabetes, the rapid administration of the test, and receipt of test results could be treated by the administration of the appropriate antidote to the given condition.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A method for measuring the level of glucose in animal body fluids comprising placing a sample of said body fluid in contact with a glucose indicator, said indicator comprising a reversible complex of a carbohydrate component, a binding macromolecular component and an indicator element associated with one of said components, maintaining said body fluid in contact with said glucose indicator for a period of time sufficient for any glucose present in said body fluid to displace said carbohydrate component in a complex with said binding macromolecular component, and for said indicator element to be released thereby to signify the presence and level of said glucose.

2. The method of claim 1 wherein said glucose indicator is provided in strip form.

3. The method of claim 2 including removing excess body fluid from said indicator after said indicator element is released.

4. The method of claims 1 or 2 wherein said binding macromolecular component comprises a binding protein, said carbohydrate component comprises a sugar selected from the group consisting of monosaccharides, oligosaccharides and mixtures thereof, and said indicator element is selected from the group consisting of color forming materials capable of forming precipitates, and mixtures thereof.

5. The method of claim 4 wherein said binding macromolecular component is fixedly attached to an inert, insoluble substance, said carbohydrate component is bound thereto in said reversible complex, and said indicator element is bonded to said carbohydrate component.

6. The method of claim 4 including the further step of comparing the activity of said indicator element after release with the results of comparative tests of said indicator element associated with given levels of said glucose.

7. The method of claim 6 wherein said indicator element is a plurality of different color forming materials, and said comparative tests are disposed on said color forming materials with specific concentrations of said glucose.

8. A glucose indicator for use in measuring the level of glucose in animal body fluids comprising,
   a reversible complex of a carbohydrate component, a binding macromolecular component, and a indicator element associated with one of said components,
   said reversible complex adapted to dissociate in the presence of glucose in said body fluid, whereby said glucose forms a complex with said macromolecular component, and said indicator element is released and signifies the presence of said glucose.

9. The indicator of claim 8 wherein said carbohydrate component comprises a sugar selected from the group consisting of monosaccharides, oligosaccharides, and mixtures thereof,
   said binding macromolecular component is selected from the group consisting of natural binding proteins, synthetic binding proteins and mixtures thereof, and
   said indicator element is selected from the group consisting of color forming materials, precipitate forming materials and mixtures thereof.

10. The indicator of claim 9 wherein said binding macromolecular componet comprises a natural binding protein, and said indicator element comprises a color-forming material, said color-forming material selected from the group consisting of dyes, color forming radicals and mixtures thereof.

11. The indicator of claim 10 wherein said binding macromolecular component comprises one or more lectins, and said carbohydrate component comprises monosaccharides and oligosaccharides containing a material selected from the group consisting of glucose, mannose and mixtures thereof.

12. The indicator of claim 11 wherein said binding macromolecular component comprises Concanavalin A, and said oligosaccharides contain up to about 6 monosaccharide units.

13. The indicator of claims 8,9,10,11 or 12 wherein said reversible complex is affixed to an inert, insoluble substrate.

14. The indicator of claim 13 wherein said substrate is prepared from a material selected from the group consisting of natural and synthetic resins, ceramic materials, and mixtures thereof.

15. The indicator of claim 13 wherein said substrate is prepared from a material selected from the group consisting of cellulose, vinyl resins, glass and mixtures thereof.

16. The indicator of claim 13 wherein said binding macromolecular component is fixedly attached to said substrate and reversibly bound to said carbohydrate component, and said indicator element is bound to said carbohydrate component.

17. The indicator of claim 13 wherein said carbohydrate component is fixedly attached to said substrate and reversibly bound to said binding macromolecular component, and said indicator element is bound to said binding macromolecular component.

18. The indicator of claim 13, wherein said substrate is in the form of a strip.

19. The indicator of claim 13 wherein said substrate bearing said reversible complex is enclosed within a membrane permeable to said body fluid and adapted to permit the passage therethrough of said carbohydrate component and said glucose.

20. A kit for measuring the level of glucose in animal body fluid comprising the glucose indicator of claim 13 in combination with comparative test results of said indicator associating the activity of said indicator element with specific levels of said glucose.

21. The kit of claim 20 wherein said carbohydrate component comprises a plurality of different oligosaccharides, each oligosaccharide associated with a color-forming material that gives a color reaction different from that of the remaining color forming materials, and said comparative test results comprise a color chart relating specific colors to particular levels of glucose concentration.

* * * * *